(12) United States Patent
Carroll et al.

(10) Patent No.: US 9,671,301 B2
(45) Date of Patent: Jun. 6, 2017

(54) SMALL-SCALE PRESSURE SENSORS

(75) Inventors: David L. Carroll, Winston-Salem, NC (US); Faith M. Coldren, Strasbourg (FR); Nicole H. Levi, Winston-Salem, NC (US); Lawrence X. Webb, Winston-Salem, NC (US); William D. Wagner, Clemmons, NC (US); Thomas L. Smith, Winston-Salem, NC (US); Brian Werner, Lancaster, PA (US); J. Baxter Mcguirt, Winston-Salem, NC (US); Manoj Namboothiry, West Lafayette, IN (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1833 days.

(21) Appl. No.: 12/443,249

(22) PCT Filed: Sep. 28, 2007

(86) PCT No.: PCT/US2007/021088
§ 371 (c)(1),
(2), (4) Date: Mar. 29, 2010

(87) PCT Pub. No.: WO2008/108820
PCT Pub. Date: Sep. 12, 2008

(65) Prior Publication Data
US 2010/0185121 A1    Jul. 22, 2010

Related U.S. Application Data

(60) Provisional application No. 60/827,489, filed on Sep. 29, 2006, provisional application No. 60/893,466, filed on Mar. 7, 2007.

(51) Int. Cl.
G01L 11/02 (2006.01)
A61B 5/03 (2006.01)
A61B 5/00 (2006.01)

(52) U.S. Cl.
CPC ............... *G01L 11/02* (2013.01); *A61B 5/03* (2013.01); *A61B 5/445* (2013.01); *A61B 2562/0247* (2013.01)

(58) Field of Classification Search
CPC .... G02F 2203/10; G01L 11/02; G01L 11/241; G01L 11/247; A61B 2562/0247; A61B 5/03–5/038
(Continued)

(56) References Cited

U.S. PATENT DOCUMENTS 4,858,620 A    8/1989  Sugarman et al.
4,918,305 A *  4/1990  Wlodarczyk et al. ... 250/227.14
(Continued)

OTHER PUBLICATIONS

Wong, C.L. and H.P. Ho. "Application of Spectral Surface Plasmon Resonance for Gas Pressure Sensing." IEEE 2002. p. 73-77.*
(Continued)

*Primary Examiner* — Adam J Eiseman
(74) *Attorney, Agent, or Firm* — Myers Bigel, P.A.

(57) ABSTRACT

The present invention provides a method of sensing pressure in a region of interest by providing a plurality of metallic particles operatively associated with one another in the region of interest (for example, wherein the metallic particles sustain a plasmon upon excitation), and with the metallic particles configured or positioned in relationship to one another so that a physical property of the particles (for example, the energy of the plasmon) varies in response to pressure; measuring the physical property of the metallic particles that varies in response to pressure; and then determining the pressure in the region of interest from the detected physical property (e.g., resistance, energy of the plasmon). Compositions, articles and formulations for carrying out the method in industrial and biomedical applications are also described.

20 Claims, 15 Drawing Sheets

(58) Field of Classification Search
USPC ....... 600/485, 486, 488, 552, 553, 561, 587, 600/593, 595
See application file for complete search history.

(56) References Cited

U.S. PATENT DOCUMENTS

| | | | |
|---|---|---|---|
| 4,932,262 A * | 6/1990 | Wlodarczyk | 73/705 |
| 7,008,559 B2 * | 3/2006 | Chen | 252/301.6 S |
| 2004/0062809 A1 * | 4/2004 | Honiger et al. | 424/486 |
| 2005/0113560 A1 | 5/2005 | Sugawara | |
| 2005/0113938 A1 * | 5/2005 | Jamiolkowski et al. | 623/23.74 |
| 2005/0169348 A1 | 8/2005 | Chen et al. | |
| 2006/0189910 A1 | 8/2006 | Johnson et al. | |
| 2008/0241262 A1 * | 10/2008 | Lee et al. | 424/490 |
| 2010/0053608 A1 * | 3/2010 | Lee | 356/326 |
| 2011/0098579 A1 * | 4/2011 | Ajiki et al. | 600/485 |

OTHER PUBLICATIONS

International Search Report and Written Opinion for PCT/US07/21088.

\* cited by examiner

SMALL-SCALE PRESSURE SENSORS

RELATED APPLICATIONS

This application is a 35 U.S.C. §371 National Phase application of International Application Serial No. PCT/US2007/021088, filed Sep. 28, 2007, which claims priority to U.S. Provisional Application Ser. No. 60/827,489, filed Sep. 29, 2006 and 60/893,466, filed Mar. 7, 2007, the disclosures of which are hereby incorporated in their entireties.

GOVERNMENT FUNDING

This invention was made with government support under grant no. FA9550-04-1-0161 from the Air Force Office of Science and Research. The US Government has certain rights to this invention.

FIELD OF THE INVENTION

This invention relates to pressure sensors, compositions and combinations containing such pressure sensors, and methods of use thereof in a variety of industrial and biomedical applications, including but not limited to implantable biomedical devices and pressure-sensing coatings.

BACKGROUND OF THE INVENTION

Acute compartment syndrome is considered a true surgical emergency, which, if not diagnosed and treated immediately, can lead to devastating disabilities, amputation, or even death (Elliott K G B, Johnstone A J: Diagnosing acute compartment syndrome. *J Bone Joint Surg* 85-B:625-632, 2003). Compartment syndrome most commonly occurs following fractures of the extremities, prolonged compression of muscle compartments, localized vascular damage, or even as a result of surgical intervention (Hargens A R et al., Tissue fluid pressures: From basic research tools to clinical applications. *J Orthop Res* 7:902-909, 1989).

While the exact pathophysiology is still debated, a compartment syndrome is said to exist when the interstitial pressure is elevated above capillary blood pressure (Hargens A R et al., Tissue fluid states in compartment syndromes. *9th Eur Conf Microcirculation* 15:108-111, 1977; Hargens A R et al., Interstitial fluid pressure in muscle and compartment syndromes in man. *Microvas Res* 14:1-10, 1977; Hargens A R, Mubarak S J: Current concepts in the pathophysiology, evaluation and diagnosis of compartment syndrome. *Hand Clin* 14:371-383, 1998). This increase in pressure results in occlusion of microarterial flow, which in turn, leads to depleted metabolic resources and impaired venous and lymphatic drainage of the affected compartment. This microvascular occlusion exacerbates the edematous process increasing interstitial pressure (ISP) and causing lymphatic collapse of the compartment; these changes eventually lead to necrosis and Volkmann's contracture of the compartmental musculature and vasculature within the affected compartment or necrosis in an affected specialized tissue or organ.

Therefore, the measurement of ISP is a valuable tool for diagnosing acute compartment syndrome. Hargens and Ballard reviewed historical and methodological approaches for measuring ISP in humans in 1995 and described the wick catheter technique, Slit Catheter Technique, Myopress Catheter, and Camino Fiber Optic Catheter. (Hargens A R, Ballard R E: Basic principles for measurement of interstitial pressure. *Oper Tech Sports Med* 3:237-242, 1995). All of these techniques, while slightly different in approach, sensitivity, and calibration, involve the insertion and maintenance of a catheter within the injured compartment in order to measure ISP. While transducer-tipped catheters were evaluated as the best current technology for measurement of ISP, the technological theory is still based on the invasive 1968 wick catheter (Crenshaw A G, Styf J R, Mubarak S J, Hargens A R: A new "transducer-tipped" fiber optic catheter for measuring interstitial pressures. *Orthop Res* 8:464-468, 1990).

Questions about the utility and prevalence of the clinical use of these catheter measurement techniques in the non-academic medical center setting have been raised. Russel, et al. described problems commonly encountered with the use of the wick catheter technique including inadequate calibration procedures and thrombosis of the catheter (Russel W L, Apyan P M, Burns R P: An electronic technique for compartment pressure measurement using the wick catheter. *Surg Gyn Obst* 2:173-175, 1985). Furthermore, the invasiveness of the current measurement procedure as well as the lack of physicians trained in the use of the equipment indicate the need for an easier, more reliable, and less invasive technique to measure compartment pressure.

SUMMARY OF THE INVENTION

A first aspect of the invention is a method of sensing pressure in a region of interest, comprising: (a) providing one or more (e.g. a plurality of) sensor particles in the region, each of the sensor particles comprising: (i) a polymer support and (ii) a plurality of metallic particles operatively associated with the polymer support and one another, optionally but preferably wherein the metallic particles sustain a plasmon upon excitation, and with the metallic particles configured so that a physical property of the particles (for example, resistance, the energy of the plasmon, e.g., detected by detecting emitted wavelength or emitted light intensity) varies in response to pressure; (b) measuring the physical property of the metallic particles that varies in response to pressure; and then (c) determining the pressure in the region of interest from the detected physical property (e.g., resistance, energy of the plasmon).

A second aspect of the invention is a pressure-sensing biomedical implant, comprising: (a) a biomedical implant substrate; and (b) a plurality of metallic particles operatively associated with the substrate and one another, optionally but preferably wherein the metallic particles sustain a plasmon upon excitation, and with the metallic particles configured so that the energy of the plasmon varies in response to pressure, and/or so that another physical property such as an electrical property of the particles (e.g., resistance) varies in response to pressure.

A further aspect of the invention is a method of sensing pressure in a subject, comprising the steps of: (a) implanting a pressure-sensing biomedical implant as described herein in a region of interest in the subject; (b) measuring a physical property of the metallic particles that varies in response to pressure; and then (c) determining the pressure in the region of interest from the detected physical property.

A still further aspect of the invention is pressure-sensing particles, the particles comprising: (i) a polymer support; and (ii) a plurality of metallic particles operatively associated with the polymer support and one another, optionally but preferably wherein the metallic particles sustain a plasmon upon excitation, and with the metallic particles configured so that the plasmon varies in response to pressure, and/or so that another physical property of the metallic particles varies in response to pressure.

A further aspect of the invention is a pharmaceutical formulation, comprising: (a) a pharmaceutically acceptable carrier; and (b) pressure-sensing particles as described herein in the carrier.

A further aspect of the invention is a pressure-sensing coating composition, comprising: (a) a film-forming resin; (b) a solvent that disperses the resin; (c) one or more (e.g. a plurality of) sensor particles dispersed therein; each of the sensor particles comprising: (i) a polymer support and (ii) a plurality of metallic particles operatively associated with the polymer support and one another, optionally but preferably wherein the metallic particles sustain a plasmon upon excitation, and with the metallic particles configured so that a physical property of the particles such as resistance or the plasmon energy varies in response to pressure; and (d) optionally, at least one pigment.

A still further aspect of the invention is a pressure-sensing article produced by the process of coating an article with a pressure-sensing coating composition as described herein, along with methods of sensing pressure on such articles by: (a) exciting the metallic particles to produce emitted light therefrom; (b) measuring a physical property of the metallic particles that varies in response to pressure; and then (c) determining the pressure in the region of interest from the detected physical property.

Figure 1:
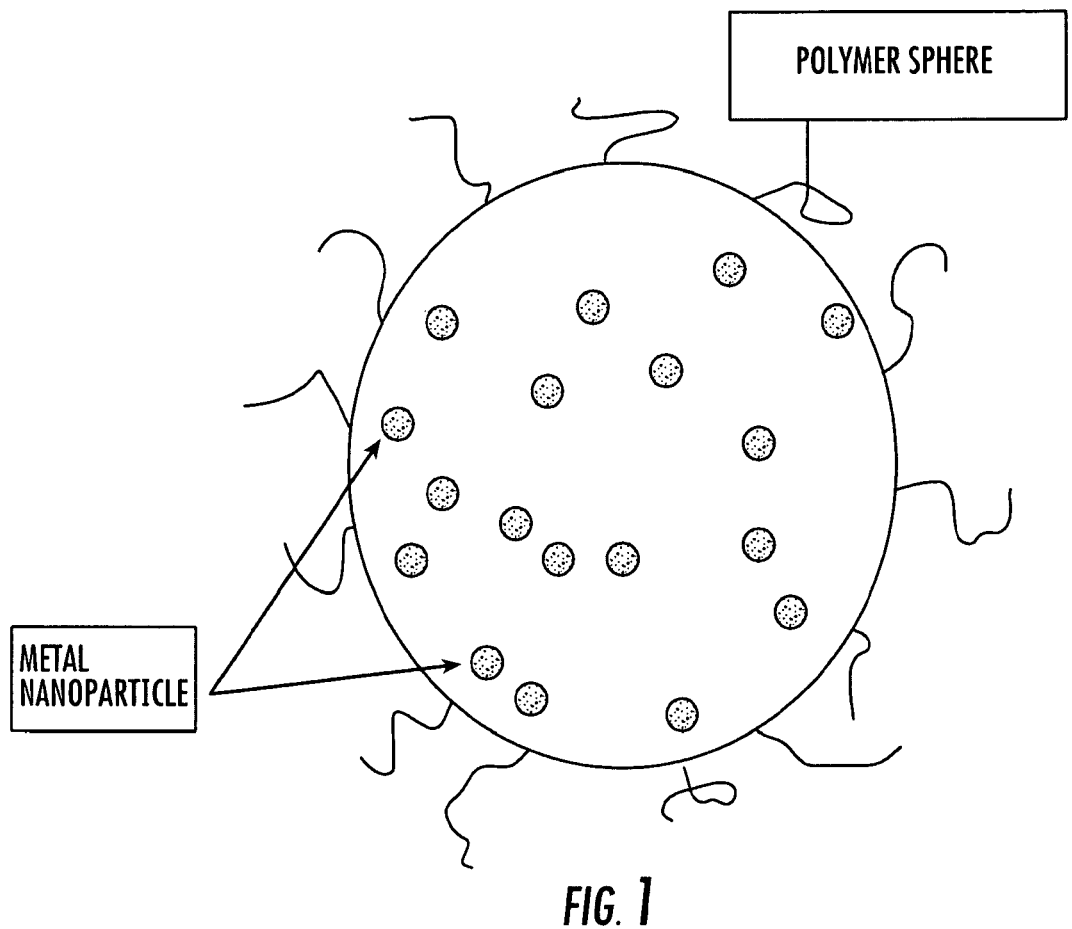
FIG. 1 is a schematic illustration of a particle device of the present invention.

The present invention is explained in greater detail in the specification set forth below. The disclosures of all U.S. Patent references cited herein are to be incorporated by reference herein in their entirety.

DETAILED DESCRIPTION OF EMBODIMENTS OF THE INVENTION

A. Definitions

"Polymers" that can be used to carry out the present invention (e.g., to form polymer pressure-sensing particles) may be natural or synthetic and may be bioabsorbable or stable, depending upon the particular application. In some embodiments the polymers are preferably physiologically acceptable or biocompatible. Suitable examples include but are not limited to chitosan, alginate, collagen, fibronectin, polylactide, polyethylene glycol, polycaprolactone, polycolide, polydioxanone, polyacrylates, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof. See, e.g., U.S. Pat. Nos. 6,991,652 and 6,969,480.

"Metals" from which metallic particles used to carry out the present invention include any metal that can sustain a surface plasmon in response to excitation (e.g., by light or electricity). Suitable examples include but are not limited to silver, gold, platinum, copper, tungsten, titanium, palladium, and alloys thereof (e.g., alloys of the foregoing with each other, and/or with other metals such as tin, e.g., a bronze alloy of copper and tin). When the metallic particles are to be implanted within a subject, the metallic particles are preferably formed from gold, silver, or alloys thereof (e.g., gold/nickel alloys).

"Polymer supports" for carrying out the present invention may be in any shape and include rods, ellipsoids, spheroids, tubes (single walled and multi-walled), and complex or combined shapes (e.g., as demonstrated by S. Chen, Z. L. Wang, J. Ballato, S. Foulger, and D. L. Carroll, "Monopod, Bipod, and Tetrapod Gold Nanocrystals", Journal of the American Chemical Society ja038927. DEC (2003)).

"Metallic particles" for carrying out the present invention may likewise be in any shape and include rods, ellipsoids, spheroids, tubes (single walled and multi-walled), and complex or combined shapes (e.g., as demonstrated by S. Chen, Z. L. Wang, J. Ballato, S. Foulger, and D. L. Carroll, "Monopod, Bipod, and Tetrapod Gold Nanocrystals", Journal of the American Chemical Society ja038927. DEC (2003)).

"Excitation" or "exciting" as used herein may be carried out by any suitable technique, such as by electrical excitation, emitted light excitation at a particular wavelength, ambient light excitation, etc.

"Compartment syndrome" as used herein refers to a condition in which increased pressure within a limited space compromises the circulation and function of the tissues within that space. See, e.g., K. Elliott et al., *J. Bone Joint Surg [Br]* 85-B, 625-632 (5 Jul. 2003). Suitable compartments include both muscle compartments (e.g., skeletal muscle, cardiac muscle, etc.) and non-muscle compartments (e.g., gut, peritoneum, kidney, cranial cavity for monitoring head trauma or closed head injury, etc.).

"Wound" as used herein includes any type of accidental or deliberate (e.g., surgical) tissue trauma, including but not limited to incisions, lacerations, ulcers, abrasions, burns, crush injuries, amputations, punctures, and combinations thereof.

"Negative pressure wound therapy" as used herein is known and describes techniques in which wound healing is facilitated by the application of a vacuum, or negative pressure, to the wound. See, e.g., U.S. Pat. No. 5,645,081 The specific modality of implementation is not critical and any of a variety of techniques can be employed, including but not limited to those described in U.S. Pat. Nos. 7,004,915; 6,951,553; 6,855,135; 6,800,074; 6,695,823; and 6,458,109.

Subjects that may be implanted with or treated by the present invention include both human subjects and animal subjects (particularly mammalian subjects such as dogs, cats, horses, pigs, sheep, cows, etc.) for veterinary purposes.

B. Pressure-Sensing Particles and Compositions Thereof

In general, pressure-sensing particles of the invention comprise, consist of or consist essentially of (i) a polymer support; and (ii) a plurality of metallic particles operatively associated with the polymer support and one another, wherein the metallic particles sustain a plasmon upon excitation. As discussed further below, the metallic particles are configured so that the plasmon varies in response to pressure, thereby permitting sensing of that pressure (as also discussed further below), and/or so that an electrical property of the particles varies in response to pressure (e.g., resistance, as pressure increases and distance between metallic particles decreases).

The polymer supports may be composed of any suitable material, particularly polymers or organic polymers (including stable polymers and bioabsorbable polymers), and composites and mixtures thereof. See, e.g., U.S. Pat. Nos. 6,942,897; 6,929,675; 6,913,825; 6,899,947; 6,888,862; 6,878,445; 6,838,486; 6,294,401; etc. For some applications the polymer supports may be coupled to (e.g., covalently coupled to) other agents such as members of specific binding pairs (e.g., proteins, peptides, antibodies, or ligands, such as antibodies to cell-surface proteins or peptides on the cells in regions of interest) depending upon the particular application thereof.

The diameters of the polymer supports will depend in part on the size of the metallic particles they carry, but can generally be from 5 nanometers up to 100 or 500 microns or more.

In general, the metallic particles may be from 1 nm to 1 micron in diameter. In particular embodiments the metallic particles can be from 1, 5 or 10 nm up to 100 or 500 nanometers in diameter, or more, though for other applications the diameters may range up to 1 microns as noted above.

The metallic particles may be configured on or within the polymer support so that their plasmon, and/or other physical property such as resistance, varies in response to pressure in a variety of ways. In general, the plasmon changes in response to pressure due to a decrease in spacing between the metallic particles as pressure increases, or an increase in distance between the particles as pressure decreases. Hence, in one embodiment, the metallic particles can be coated on the surface of the polymer support so that spacing between particles decreases as the support is crushed. In another embodiment, the particles are dispersed within a polymer material and the support formed therefrom with the metallic particles distributed throughout. In some embodiments a uniform distribution is preferred, so that the light signal generated by the sensors in response to pressure is more uniform, or has a greater amplitude at a particular predetermined wavelength. In some embodiments, the metallic particles can be pre-coated with a polymer (which may be the same or different from the polymer from which the support is formed) or pre-coated with a film-forming material, self-assembled monolayer, or the like, so that the particles cannot directly contact one another and more uniform spacing is achieved. Thin metal shell coatings may also be used, e.g., nanoshells having a dielectric or silica core and a metallic coating.

An illustrative embodiment of sensor particles of the invention is schematically illustrated in FIG. 1. As shown therein, the sensor is built from a polymer sphere of any composite and DIA of 5 nm to 100 micron. Into this polymer sphere is placed nanoparticles of metals. The metals can be any metal with metals that have specific plasmonic resonances preferred. The diameter can be any diameter that allows for filling within the sphere, with the diameter that yield the desired readout wavelength preferred. The metal nanoparticles emit specific wavelengths of light based upon their plasmon resonances. This requires that the size distribution be relatively narrow, but this is available commercially. When the sphere is compressed, the particle density changes and the plasmon resonances shift their emission. This is due to a change in the surrounding dielectric function (on average).

For some uses the particles can be distributed in or carried in a pharmaceutical formulation. The formulation typically comprises, consists of or consists essentially of (a) a pharmaceutically acceptable carrier (such as an aqueous carrier, including emulsions, suspensions, dispersions, etc.); and (b) pressure-sensing particles as described above. In such an embodiment the pressure sensing particles can be injectable (e.g., sized to pass through an injection syringe or needle) and are preferably formed from pharmaceutically acceptable polymers and metals.

C. Uses of Pressures-Sensing Particles

A method of sensing pressure in a region of interest can, in general, be carried out by: (a) providing one or more (e.g. a plurality of) sensor particles as described above in that region; (b) measuring a physical property of the metallic particles that varies in response to pressure; and then (c) determining the pressure in the region of interest from the detected physical property.

In some embodiments, the measuring step (b) is carried out by: (i) exciting the sensor particles to produce emitted light therefrom; (ii) detecting a property of the emitted light (e.g., intensity, wavelength), wherein the property varies in response to the energy of the plasmon (such as a surface plasmon). The exciting step can be carried out by any suitable means, such as by electrical or light excitation.

In other embodiments, the measuring step (b) is carried out by: (i) passing a current through the metallic particles; (ii) detecting the resistance of the metallic particles, wherein the resistance decreases in response to an increase the pressure. In this embodiment the determining step (c) is carried out by determining the pressure in the region of interest from the detected resistance. Measurement conditions are not critical. The current can be small, e.g., from 10 to 500 nanoAmps, at 1-10 volts. Any suitable measuring device can be used, such as a Keithly digital voltmeter.

Any suitable pressure can be sensed by constructs of the invention (particles, or other constructs, such as implants or painted/coated articles as discussed below), depending on whether they are used in vivo or ex vivo (e.g., in industrial applications as discussed below). For example, the pressure to be sensed may be from −5000 or −1000 to 1000 or 5000 torr. In some embodiments, the pressure to be sensed may be from −100 to 100 or 200 torr; in some embodiments the pressure to be sensed may be from −300 to 300 torr.

The wavelength of the emitted light from the particles may be between 2000 and 200 nanometers or in some embodiments between 1000 and 200 nanometers. When light is used to excite the particles the wavelength of the excitation light is preferably different from the wavelength of the emitted light. When the particles, or metallic particles, are implanted within a human or animal subject, the excitation and emission wavelengths are preferably selected so that they readily pass through the tissue (e.g., light in the red region of the spectra). Thus in some embodiments, when the particles are implanted in a tissue, the wavelength may be between 1000 and 700 nanometers.

Particular apparatus for excitation and detection is not critical. While custom devices can be readily made by those skilled in the art (e.g., devices including both excitation source, emission detector, and circuitry configured to convert a detected wavelength to a quantitative indication of pressure), hand-held lights and standard spectrophotometers can also be used.

As indicated above, in some embodiments the region of interest is in a human or animal subject. Suitable regions include, but are not limited to, tissues, airway spaces (e.g., the surface thereof, where the particles can be administered by inhalation), vessel lumens such as blood vessel lumens, aneurisms, embolisms, joints (including but not limited to synovial joints to determine inflammation therein), etc. For such applications, the polymer support preferably consists essentially of a pharmaceutically acceptable and bioerodable polymer, the metallic particles are pharmaceutically acceptable, and the metallic particles are preferably configured (that is, are of a size and shape) so that they are excretable through the kidney of the subject. Of course, in other embodiments both the polymer support and metallic particles can be pharmaceutically acceptable, but the polymer support can be inert or stable rather than in bioerodable.

For some applications of the present invention, the region of interest is a tissue compartment in a patient suspected of compartment syndrome. The particles can be administered to any suitable (typically fascia-covered) compartment by any suitable means, such as injection.

In some embodiments the region of interest is a wound site or a region adjacent the wound site in a patient afflicted with that wound. The subject or patient may be undergoing treatment with negative pressure wound therapy. The present invention can be advantageously implemented with negative pressure wound therapy for a number of reasons. In one example, where the size or expanse of the region to be treated is not readily apparent or well-defined, the region of interest can be a region adjacent a wound site and wherein the wound is treated with negative pressure wound therapy; the method further comprising: determining the presence or absence of pathological pressure at region adjacent the wound site from the determined pressure; and treating the region adjacent the wound site when a pathological pressure therein is determined. In another example, where the ambient pressure surrounding the patient may fluctuate and hence adversely effect the therapy (e.g., at high altitudes due to a mountaineering injury, during air transport of an injured patient, etc.), the method may further comprise determining the pressure at the wound site or region adjacent the wound site to determine an actual wound pressure; and then adjusting vacuum applied to the wound in the negative pressure wound therapy in response to the actual wound pressure to enhance the efficacy of the negative pressure wound therapy.

D. Biomedical Devices and Uses Thereof

A further aspect of the invention is a pressure-sensing biomedical implant. Such an implant comprises: (a) a biomedical implant substrate; and (b) a plurality of metallic particles operatively associated with the substrate and one another, wherein the metallic particles sustain a plasmon upon excitation, and with the metallic particles configured so that the plasmon varies in response to pressure. Configuration may be achieved in like manner as described above, although polymer supports are optional and not essential when the metallic particles are carried by the substrate (e.g., the metallic particles can be molded therein or coated therein by means of a paint or coating composition, as described below).

Any suitable implant can be coated or impregnated with (in whole or in part), or otherwise carry, metallic particles as described herein to provide a pressure sensing implant, including but not limited to stents, fasteners, ports, catheters and guides, tissue scaffolds, tissue grafts such as aortic grafts, etc. In some embodiments, the biomedical implant is minimally invasive. For example, the device can be removably inserted into a blood vessel or other tissue.

Pressure sensing can be carried out in like manner as described above by (a) implanting (removably or non-removably) the pressure-sensing biomedical implant in a region of interest in the subject; (b) measuring a physical property of the metallic particles that varies in response to pressure; and then (c) determining the pressure in the region of interest from the detected physical property. In some embodiments, the measuring step (b) is carried out by: (i) exciting the sensor particles to produce emitted light therefrom; (ii) detecting a property of the emitted light (e.g., intensity, wavelength), wherein the property varies in response to the energy of the plasmon. The exciting step can be carried out by any suitable means, such as by electrical or light excitation. In other embodiments, the measuring step (b) is carried out by: (i) passing a current through the metallic particles; (ii) detecting the resistance of the metallic particles, wherein the resistance decreases in response to an increase in the pressure. In this embodiment the determining step (c) can be carried out by determining the pressure in the region of interest from the detected resistance.

Figure 14:
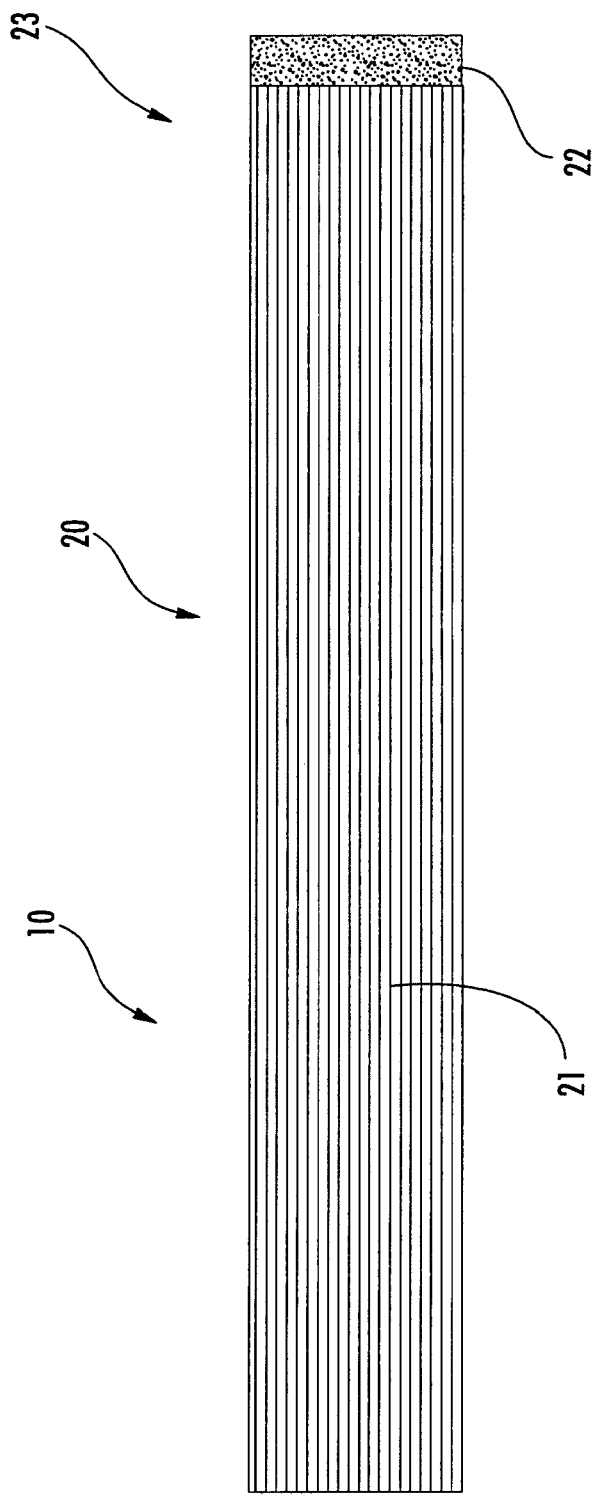
FIG. 14 is a schematic illustration of a catheter device according to embodiments of the present invention.

Biomedical devices according to embodiments of the present invention can include implantable devices, probes, and/or other devices. As schematically illustrated in FIG. 14, a fiber optic probe 10 according to embodiments of the present invention includes a body 20 formed of fiber optic fibers 21 and a tip portion 23 (the "distal portion") coated with particles 22 as described herein. In some embodiments, the probe is a device that is configured for insertion into the body, such as an interluminal device (e.g., a catheter), a device that can be inserted into tissue (e.g., muscle tissue, cardiac tissue, or other body tissues) or a subcutaneously insertable device. The coating can be carried out by any suitable technique, such as by simply painting a fiber optic fiber with a coating composition as described herein, by depositing the particles on the top and then covering the particles with a protective sheath or coating, etc. In use, the fiber optic probe can be sheathed in a protective coating, and (if desired) passed through a cannula, needle, or other guide tube to reach the desired destination. Once the tip portion is inserted into the desired location of a subject (e.g., muscle tissue, blood vessel or other body compartment or tissue), light from a suitable source such as a laser light source operatively associated with the proximal end of the fiber can be transmitted through the fiber optic fibers to the particles, and light emitted from the particles (and transmitted back down, or returned, through the fiber optic fibers) can be detected through a suitable detector operatively associated with the proximal end of the fiber.

The metallic particles 22 may be formed as a thin film on the tip of a fiber-optic 21 for use in local pressure measurements and extraction, for example, in a human or animal subject. In particular embodiments, the particles 22 may be blended into a composite structure comprising polymers, such as PLGA, PMMA, Chitosan, Collagen, elastin, or other suitable biocompatible polymer. The nanometals may be between about 1 nm to 500 nm in diameter and composed of, e.g., Ag, Au, Cu, Pt, or any other metal in which a plasmon response can be obtained. This composite material may be added to the tip of the fiber optic 21. The fiber optic 21 is typically composed of an optically transmissive core, such as a glass fiber or plastic fiber core, with an outer cladding for structural stability. In some embodiments, a portion of the core is exposed (e.g., the outer cladding is removed) such that the core comes in contact with the metallic particles 22 (which may be provided as part of a composite material). Alternatively, the metallic particles 22 and/or composite material can be added directly to the outer cladding provided the cladding is transparent.

Figure 15:
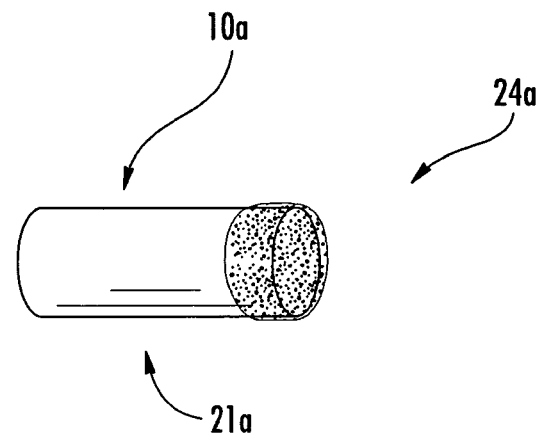
FIG. 15 is a schematic illustration of a fiber optic device according to embodiments of the present invention.

For example, as shown in FIG. 15, a device 10a includes a fiber 21a. The fiber 21a can be dipped into a polymer solution (including the metallic particles) and solvents can be allowed to dry on the fiber to form a polymer coating 24a. The polymer coating 24a may distribute the metallic particles in a random and/or disordered pattern to form a pressure sensitive paint at the end of the fiber 21a.

Figure 16:
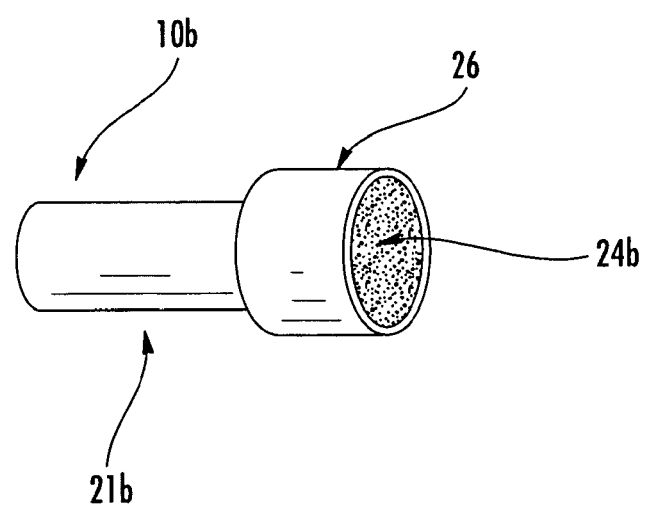
FIG. 16 is a schematic illustration of another fiber optic device according to embodiments of the present invention.

As shown in FIG. 16, a device 10b includes a polymer coating 24b (including the metallic particles) that is added to a fiber 21b through dipping processes, spraying processes, or any other suitable process or processes. An outer coating 26 is added around at least a portion of the polymer coating 24b that allows confinement of the light around the fiber 21b. Dimensional changes due to pressure on the outer coating 26 leads to the compression of the composite polymer coating 24b and an optical shift or color change. Because of the confining geometry of the outer coating 26, the sensitivity to the optical shift may be increased. The outer coating 26 may be a metal sheath formed of Au, Ag, Cu, Pt, W, or any other suitable material, such as a material which can be used to provide a mirrored surface.

In FIGS. 15-16, a portion of the fiber 21a, 21b is coated with the metallic particle coating 24a, 24b. The coating 24a, 24b may have a length from between about one micron or less to several centimeters or more. In some embodiments, the entire length of the fiber 21a, 21b can be coated, which would result in sensing pressure along the length of the fiber 21a, 21b rather than locally or at a small localized region.

Pressure sensors according to embodiments of the present invention employ the nanoparticle/biopolymer composite material described herein which absorbs light in the near-IR, where absorption bands may be detected through human bone and/or soft tissue. An increase in compartment pressure may cause the polymer to compress and the absorption bands to shift wavelength. The fiber optic based device can include bundles of fibers to define a probe or a single optical fiber can be used. As illustrated in FIGS. 14-16, fiber optic based devices may allow localized pressure measurement using fibers of 0.1 mm or less with minimal external cabling. The devices illustrated in FIGS. 14-16 may allow for low impact, rapid, and accurate diagnosis of compartment syndrome as well as other pressure-related conditions.

Figure 17:
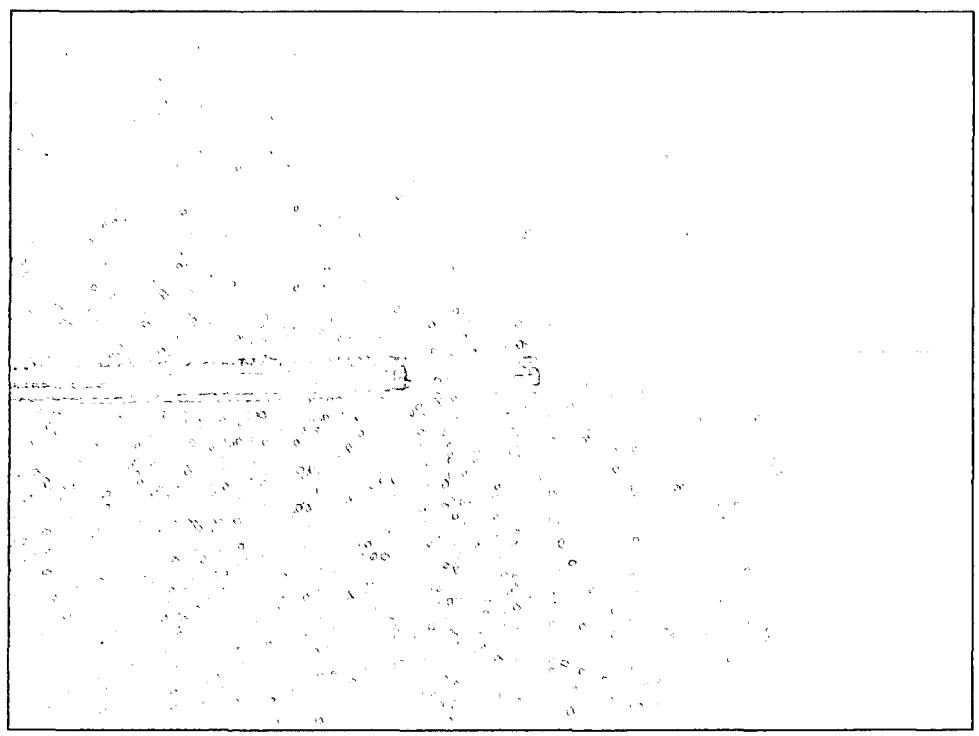
FIG. 17 is a digital image of a fiber-optic device according to embodiments of the present invention.

FIG. 17 is an image of a fiber-optic pressure sensor including a nanoparticle/biopolymer composite forming a thin film on the end of an optical fiber according to embodiments of the present invention.

Although certain embodiments according to the present invention are discussed herein with respect to fiber optic devices, such as probes or catheters (for example, in FIGS. 14-17), it should be understood that the metallic particles and/or composite materials including the particles described herein can be used as a coating or other component of various types of medical devices, for example, to detect pressure at locations in the body. In addition, the fiber optic devices described herein can be incorporated as part of another medical device. Medical devices according to embodiments of the invention (including coated fiber optic devices or other coated devices) can be inserted into the body acutely/briefly or, in some embodiments, may be chronically implanted.

E. Polymer Compositions

According to some embodiments of the invention, the nanoparticles described herein can be included into a polyimide, polyurethane or other foam material including pockets of compressible air or other gaseous/liquid materials. The foam material can include pockets of compressible fluid separated by relatively narrow filaments of material. Accordingly, the foam material may experience a greater compression than a non-foam bulk material under a similar pressure. The nanoparticles in a foam pressure sensor can generally be packed more tightly when exposed to pressure than nanoparticles in a corresponding non-foam bulk material. Without wishing to be bound by theory, there may be greater interactions between the nanoparticles' associated plasmons in a foam material, which can lead to a larger shift in the plasmon resonance bands corresponding to a larger shift in the absorption spectra of the sensor. Thus, the nanoparticles can be embedded in a foam matrix, and in some embodiments, a greater pressure sensitivity and/or a more easily detected plasmon shift in the measured absorption spectra can be obtained.

According to further embodiments of the invention, the nanoparticles described herein can be embedded in a piezoelectric polymer, such as polyvinylidene fluoride (PVDF), which can be poled during assembly. This poling makes PVDF a piezoelectric material, e.g., a material in which a stress, such as exposing the polymer to pressure, induces a potential across the material. Within the material, an electric field is then present. When the nanoparticles are excited by light and a plasmon is induced, the electric field interacts with the plasmon. The interaction can cause a shift in the plasmon resonance, and consequently, a corresponding shift in the absorption spectra of the nanoparticle/PVDF composite material. Since the mechanism of the plasmon resonance shift depends primarily on the strength of the electric field generated by the piezoelectric material, and not on the distance between the individual nanoparticles, a pressure sensor made in this fashion can experience an increased shift in the plasmon resonance.

F. Composite Pressure Sensors

Figure 21:
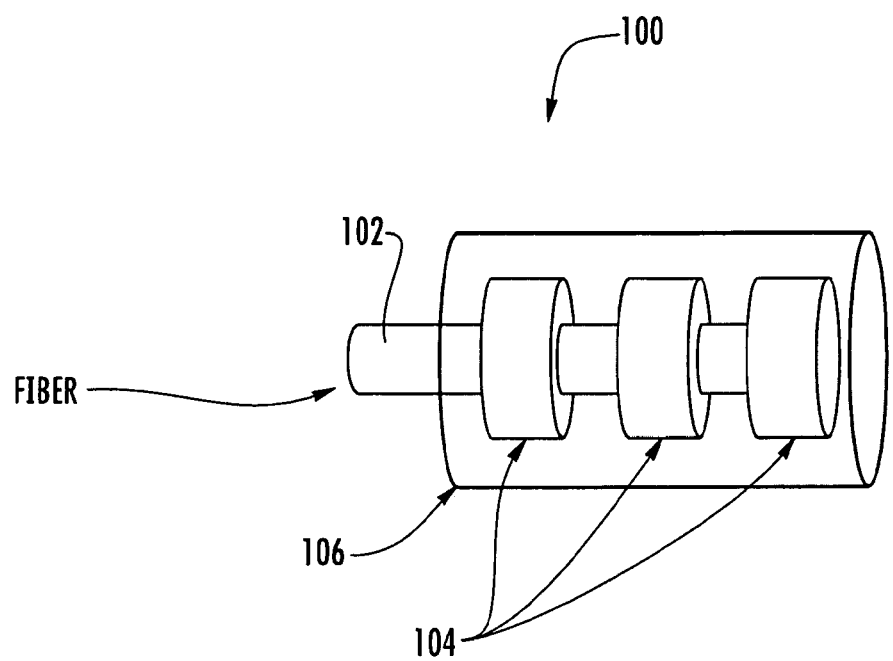
FIG. 21 is a pressure sensor device according to embodiments of the present invention including a plurality of pressure sensing transducers.

In further embodiments according to the invention, a fiber-based pressure sensor can combining several transducers on one fiber tip/end, each of which is active over specific pressure ranges. For example, as shown in FIG. 21, a device 100 includes an optical fiber 102, a plurality of nanocomposite transducers 104 and a protective sheath 106. The transducers 104 can each include a nanoparticle as described herein that is embedded in a polymer. The transducers 104 can each include different nanoparticles and/or polymers that exhibit activity or sensitivity over different pressure ranges. For example, each of the transducers 104 can include nanoparticles embedded in a foam, a crosslinked PLGA, or a chitosan transducer, respectively. In this example, the foam would generally have a very low bulk modulus (1-10 mmHg), and the PLGA would generally be active over a medium range of pressures (10's of mmHg to 100 mmHg). The high modulus chitosan would generally be active over 100's of mmHg. In this configuration, the device 100 can yield high sensitivity at low pressures and yet have a dynamic range, which extended over orders of magnitude.

Although the device 100 is illustrated with three transducers 104, it should be understood that one, two, three or more transducers 104. Each of the transducers 104 can include nanoparticles embedded in a material, and the nanoparticles and/or materials can be selected to provide pressure sensing capabilities over different ranges.

A plurality of different nanocomposite transducers 104 with different sensitivities can be utilized such that each composite includes nanoparticle chromophores that emit in different wavelength range such that it is possible to multiplex the resulting signals. For example, the nanoparticles in the transducers 104 can have different sizes so that the signals from each of the transducers 104 can be distinguished from one another. For example, the foam may have red emitter nanoparticles (e.g., particles that are about 10 nm in diameter), the PLGA may include green emitter nanoparticles (e.g., particles that are about 6 nm in diameter), and the chitosan can include blue emitter nanoparticles (e.g., particles that are about 4 nm in diameter). It should be understood that the particle sizes discussed above are examples, and the actual diameters may depend upon the composition of the particles (i.e., Au vs. Ag).

Figure 22:
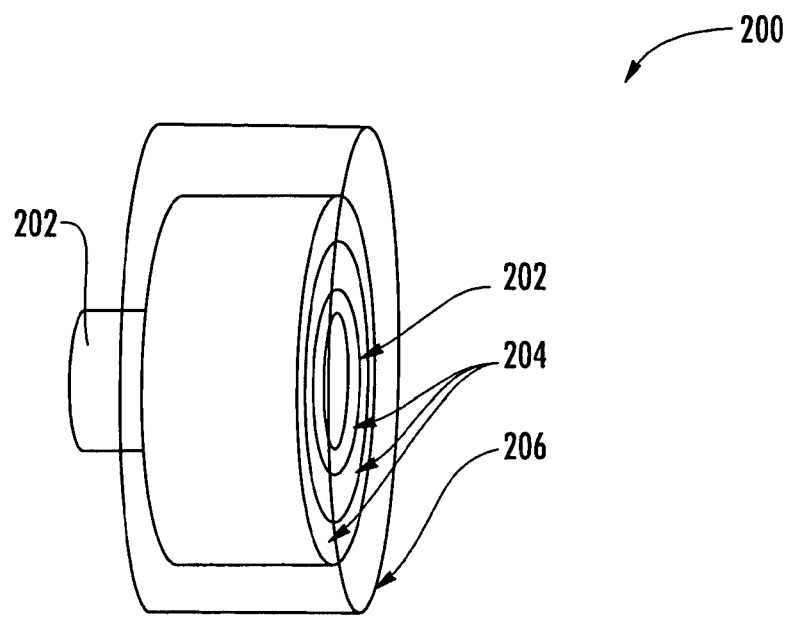
FIG. 22 is a pressure sensor device according to further embodiments of the present invention including a plurality of pressure sensing transducers.

Alternatively, this architecture might include more than three layers or may present the layers one on top of the other instead of isolated individually along the fiber strand. For example, as illustrated in FIG. 22, a device 200 includes a fiber 202, a plurality of nanocomposite transducer rings 204 and a protective sheath 206. The rings 204 can each include a different types/sizes of nanoparticles and/or materials in which the nanoparticles are embedded to provide different pressure sensitivity ranges.

According to further embodiments of the present invention, "holey" or "connected" foam materials can be implemented using either non-compressive or compressive materials as a scaffolding structure to hold the chromophore nanoparticles in place. Surface treatment of the pores in such materials can change the overall wetting behavior of a liquid into the pores and thus modify the pressure required for invasion of the pores by a liquid. For example, as illustrated in FIG. 23, a device 300 includes an Al2O3 porous templates 302 in which a hydrophobic ligand has been added to the surface to provide coated apertures 304 to hold chromophore nanoparticles 306 in position.

Figure 23:
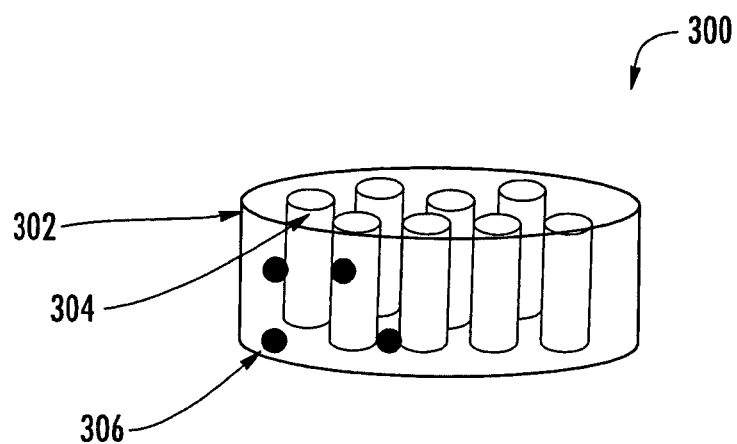
FIG. 23 is a pressure sensor device according to further embodiments of the present invention including an array of apertures.
Figure 24:
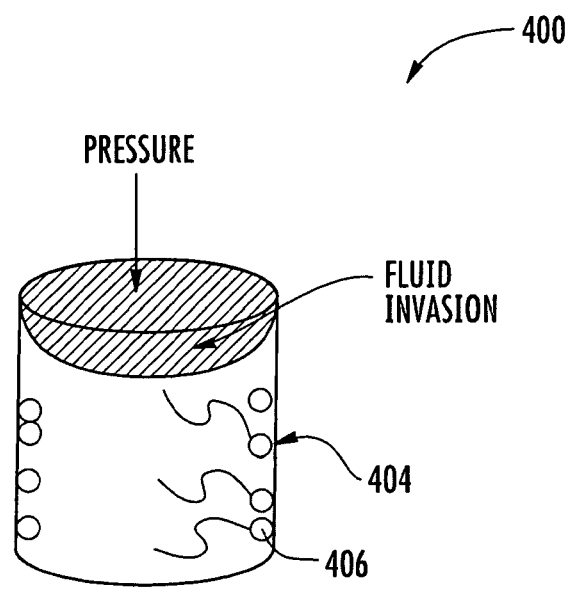
FIG. 24 is a pressure sensor device according to further embodiments of the present invention including randomly distributed apertures.

The pores or apertures 304 can be arrayed (as in the case of Alumina templates as shown in FIG. 23). Alternatively, as illustrated in FIG. 24, a device 400 can include randomly distributed apertures 404 with ligands 406 attached thereto. The apertures 404 may be formed in an interconnected porous media or foam. By placing a hydrophobic species within the pores or apertures 404, bound to the pore wall, the pressure necessary to press the liquid into the pore varies. The more hydrophilic, the more pressure is required. This is generally related to the pore size as well. For example, the pore diameters can be about 5 nm to 200 nm and the pore lengths can be about 1 nm to 1 mm. In particular embodiments, the pore diameter is about 20 nm and the pore length is about 100 microns. Alkane chains with thiol terminal groups may be a possible binding system for the pore coating. However, any suitable coating can be used, including any alternating polyelectrolyte deposition (APD), carbon nanotubes, fullerenes, etc.

With invasion of the liquid and increased pressure as illustrated in FIG. 24, the local dielectric of the piece changes making the frequency of the particles shift accordingly. The sensitivity of the device 400 can depend on various factors, including the pore size and the pore coating.

G. Coating Compositions and Uses Thereof

Coating compositions as used herein are generally known. Any of a variety of organic and aqueous coating compositions, with or without pigments, may be modified to contain sensor particles as described herein, including but not limited to those described in U.S. Pat. Nos. 7,109,262; 6,964,989; 6,835,459 (conductive paints); 6,677,035; 6,528,580; 6,235,812; etc.

In general, the compositions comprise a film-forming resin, an aqueous or organic solvent that disperses the resin; and (for present purposes optionally but preferably) at least one pigment. Other ingredients such as colorants, secondary pigments, stabilizers and the like can be included if desired. However, the compositions further comprise one or more (e.g. a plurality of) sensor particles as described herein, which may be carried by or dispersed in the solvent and/or resin, so that the sensor particles are dispersed or distributed on the surface an article coated with the composition.

Any suitable article can be coated, in whole or in part, with a composition of the invention. Suitable articles include but are not limited to automobiles and airplanes (including surfaces such as wing and propeller surfaces for aerodynamic testing), vessel hulls (including interior and exterior surfaces thereof), pressure vessels (including interior and exterior surfaces thereof) biomedical implants as described above, etc. Coating of the article with the composition can be carried out by any suitable means, such as by brushing, spraying, electrostatic deposition, dip coating, doctor blading, etc.

Pressure sensing can be carried out on an article coated with a composition as described herein again in like manner as described above by: (a) exciting the sensor particles now coated on the article to produce emitted light therefrom; (b) measuring a physical property of the metallic particles that varies in response to pressure; and then (c) determining the pressure in the region of interest from the detected physical property. In some embodiments, the measuring step (b) is carried out by: (i) exciting the sensor particles to produce emitted light therefrom; (ii) detecting a property of the emitted light (e.g., intensity, wavelength), wherein the property varies in response to the energy of the plasmon. The exciting step can be carried out by any suitable means, such as by electrical or light excitation. In other embodiments, the measuring step (b) is carried out by: (i) passing a current through the metallic particles; (ii) detecting the resistance of the metallic particles, wherein the resistance decreases in response to an increase in the pressure. In this embodiment the determining step (c) can be carried out by determining the pressure in the region of interest from the detected resistance.

While the present invention has been described with reference to a plasmon or surface plasmon on the metal particles above, it will be appreciated that, where the physical property to be measured is not a light emission property but, for example, an electrical property such as resistance, then the plasmon, or metals that sustain a plasmon, are not essential, so long as the particles are configured so that the property such as resistance changes in response to pressure.

The present invention is explained in greater detail in the following non-limiting Examples.

EXAMPLES

Measurement of Density Effects on Plasmon Emission for Embedded Ag Nanoparticles Using 5 nm DIA Ag nanoparticles we have measured a shift of 20 nm in the emission peak maximum (measured with a standard Ocean Optics spectrometer, this maximum is around 500 nm) with a change in particle density of 0.166 mg/mL to 0.50 mg/mL. These densities were blended into a transparent polymer host for measurement.

For compression of a sphere of polymer (such as PLGA) as above:

$$M_{ag} = \text{density}_{initial} 4/3\pi(r_{initial})^3 = \text{density}_{final} 4/3\pi(r_{final})^3$$

So:

$$\text{Density}_{initial}/\text{Density}_{final} = (r_{final}/r_{initial})^3$$

Based on data:

0.166/0.50=0.332 the cube root=0.692

And $(0.692)r_{initial}=r_{final}$ will give a 20 nm optical shift.

In our example we have used PLGA with a bulk modulus of 60 kPa.

Bulk Modulus $B=\Delta P/(\Delta V/V_o)$

Giving:

$\Delta P/(V_{initial}-V_{final})/V_{initial}=\Delta P/(1-V_f/V_i)=\Delta P/0.668=60000$ Pa=40 kPa For a 2 nm shift, easily within a standard instruments resolution, this number drops to ~4 kPa. This sensitivity is sufficient for the measurement of venous pressure within tissues.

Additional data illustrating various embodiments of the present invention is set forth in FIGS. 2-13.

Figure 2:
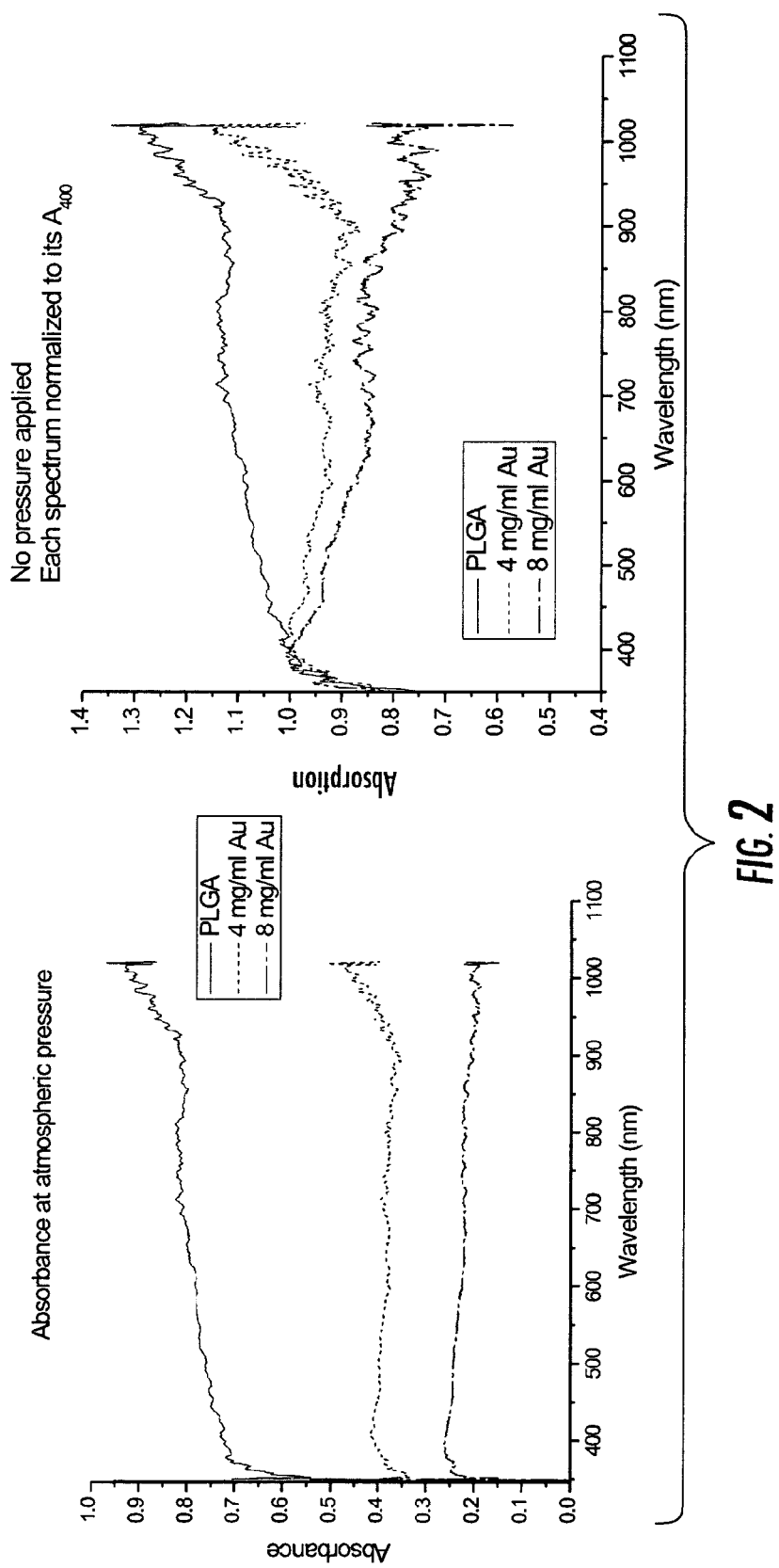
FIG. 2 is a graph of the absorbance as a function of wavelength (nm) illustrating a shift in absorbance as a density of nanoparticles is increased.

FIG. 2 shows a shift in absorbance as density of nanoparticles is increased.

Figure 3:
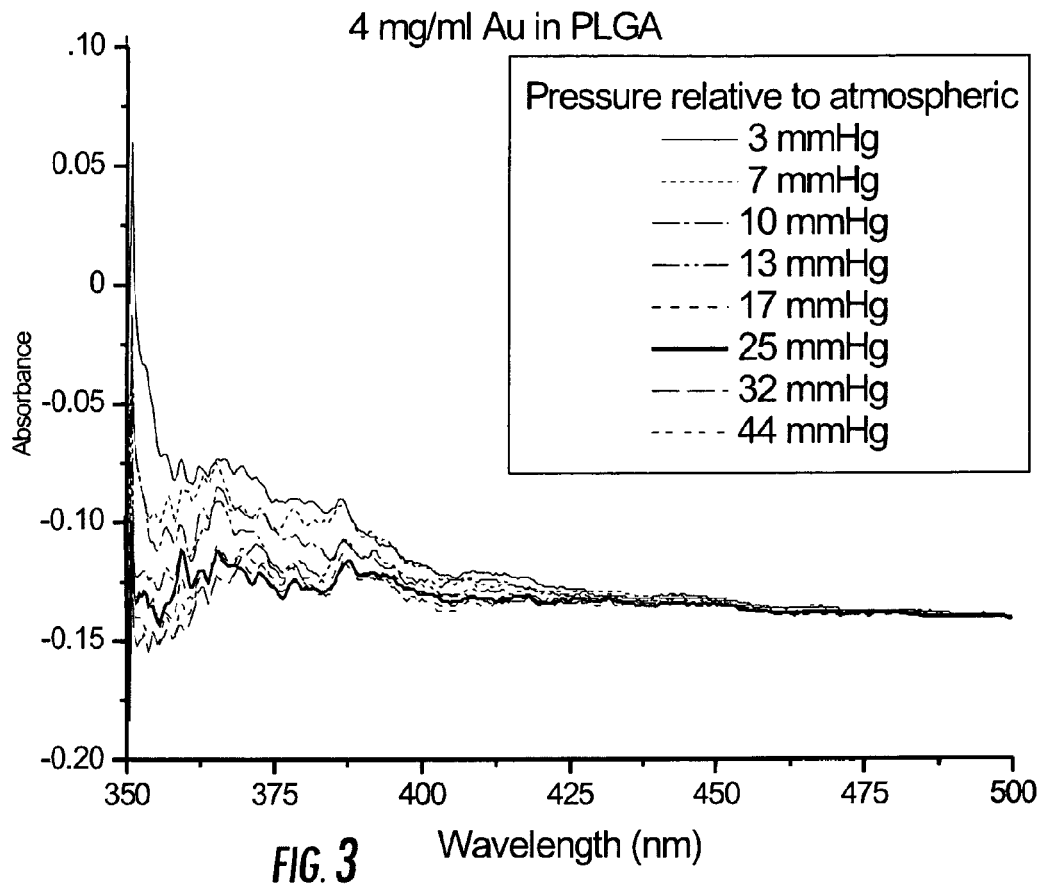
FIG. 3 is a graph of the absorption of 4 mg/ml Au in PLGA as a function of wavelength (nm).
Figure 4:
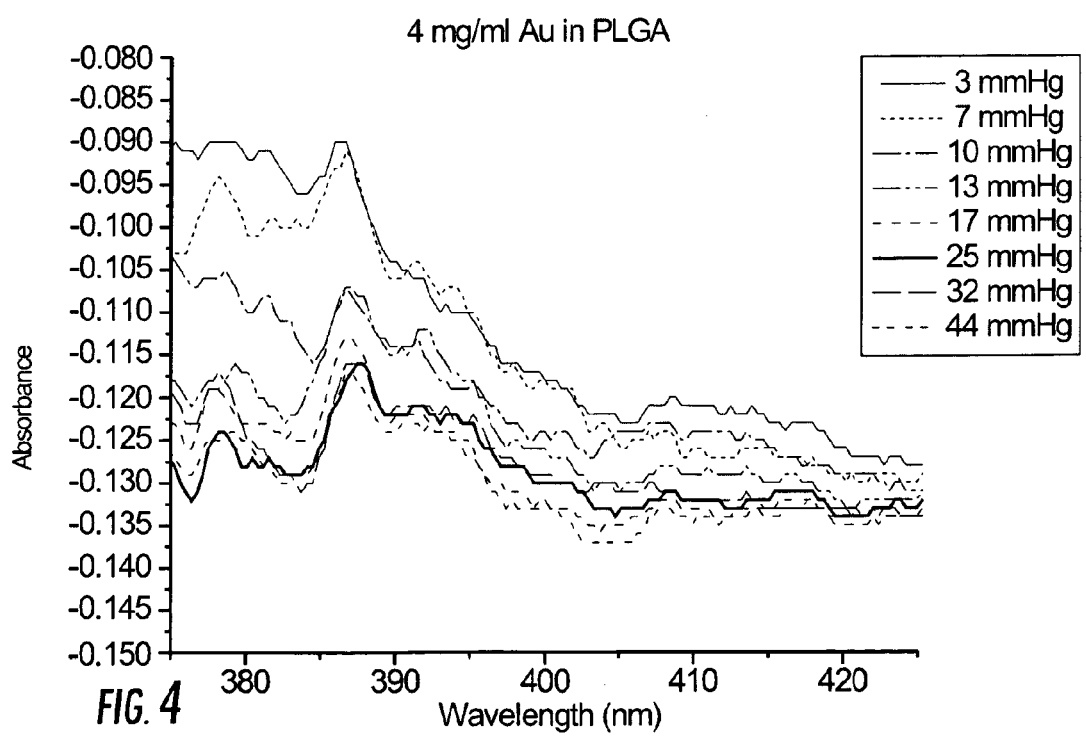
FIG. 4 is a graph of the absorbance of 4 mg/ml Au in PLGA as a function of wavelength (nm).
Figure 5:
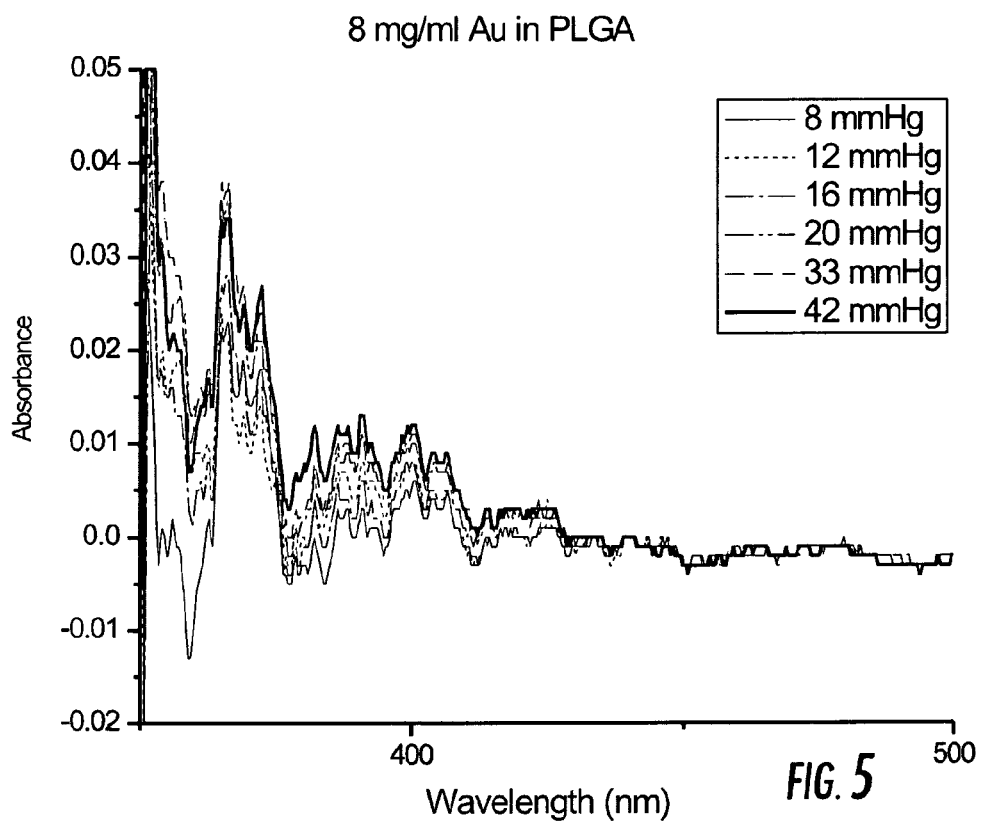
FIG. 5 is a graph of the absorbance of 8 mg/ml Au in PLGA as a function of wavelength (nm).
Figure 6:
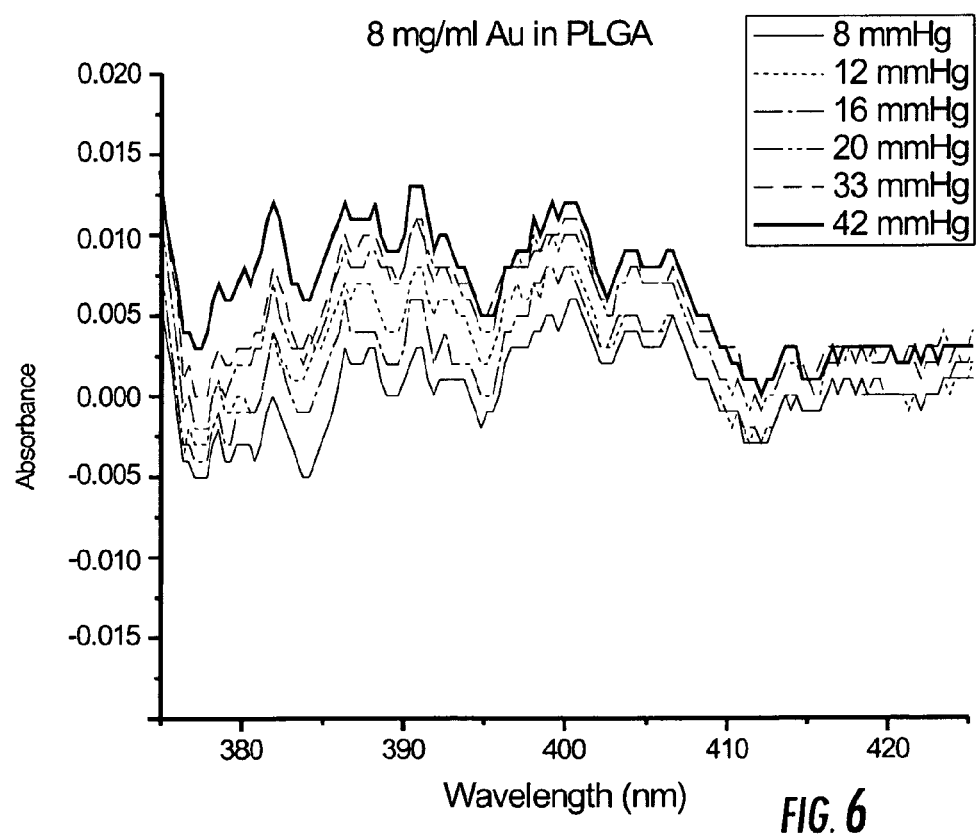
FIG. 6 is a graph of the absorbance of 8 mg/ml Au in PLGA as a function of wavelength (nm).

FIG. 3 shows absorbance of 4 mg/ml Au in PLGA; FIG. 4 shows absorbance of 4 mg/ml Au in PLGA; FIG. 5 shows absorbance of 8 mg/ml Au in PLGA; FIG. 6 shows absorbance of 8 mg/ml Au in PLGA.

Figure 7:
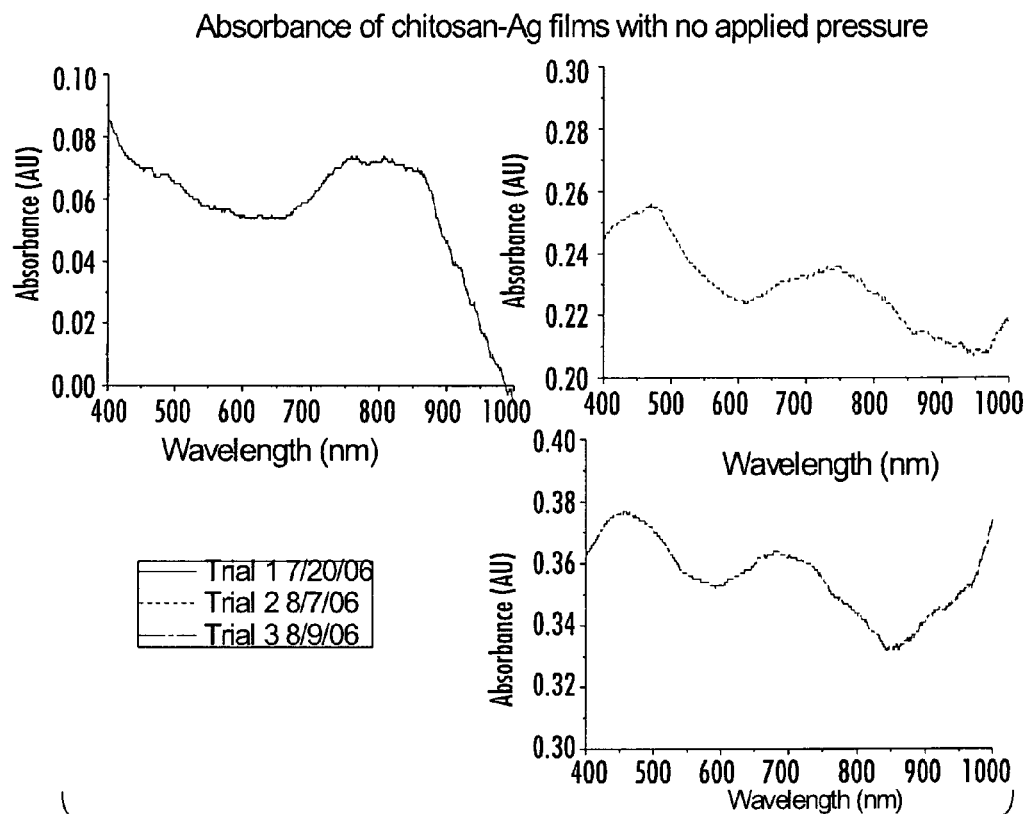
FIG. 7 is a graph of the absorbance of chitosan-Ag films with no applied pressure as a function of wavelength (nm).

FIG. 7 shows the absorbance of chitosan-Ag films with no applied pressure. These data show that we have the ability to tune nanoparticle peak absorption. Nanoparticles in (a) are different from those in (b) and (c). Note that the position of higher energy peak seems to be independent of pressure.

Figure 8:
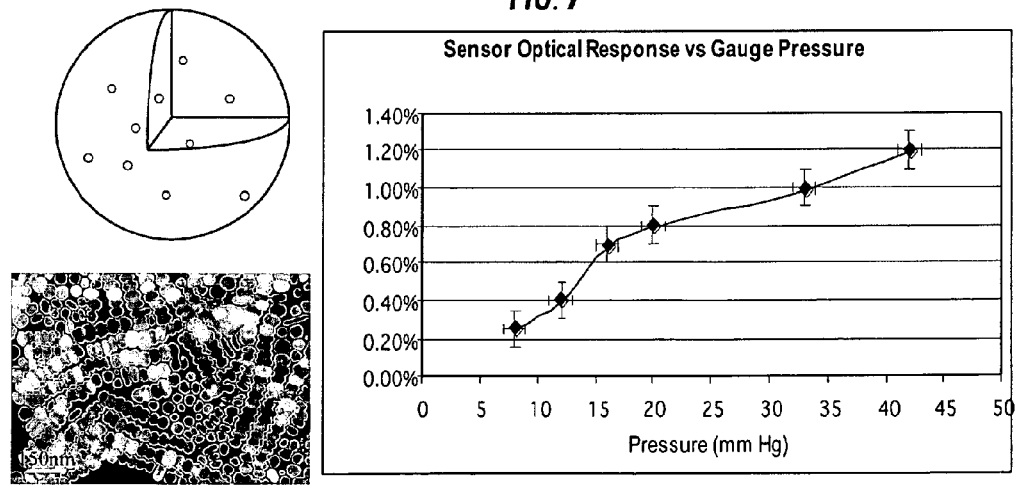
FIG. 8 is a graph of PLGA nanoparticle data for low pressures using data above to determine an optical signal shift as a function of pressure (mm Hg).
Figure 9:
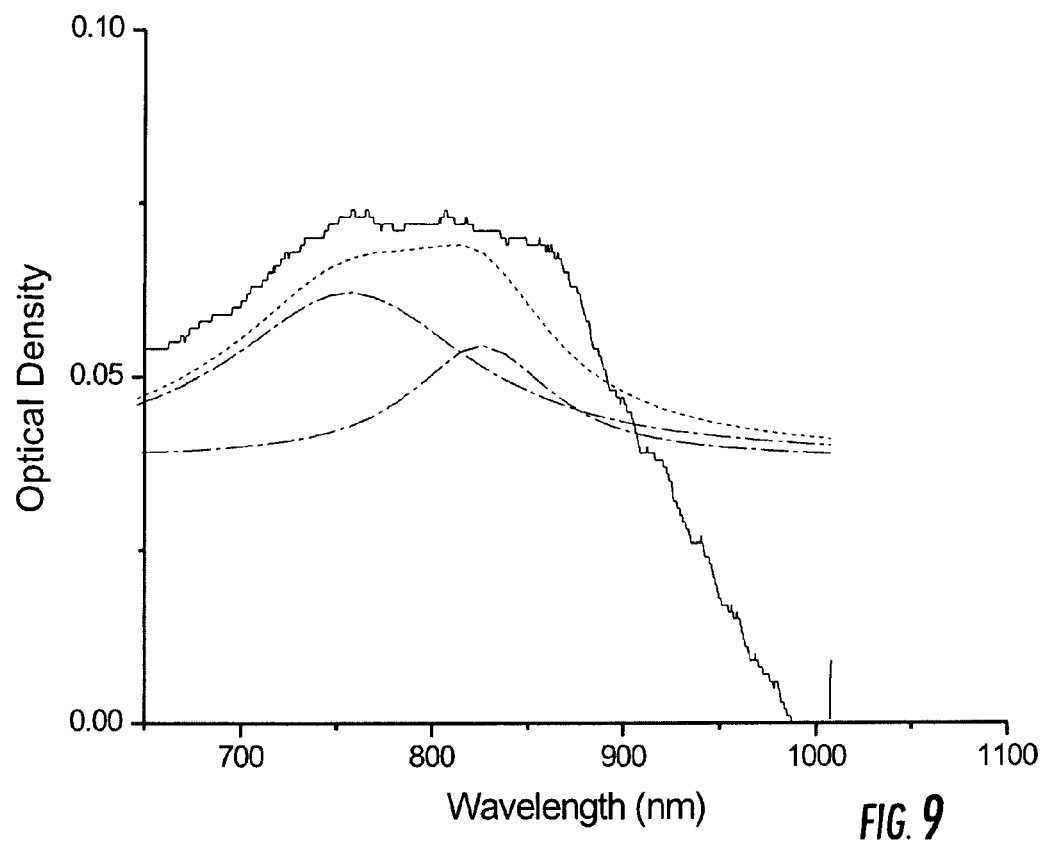
FIG. 9 is a graph of the optical density as a function of wavelength (nm) for 0.75 mg of Ag nanoparticles in chitosan at a final concentration of 2.18% (w/v). The low energy peak was decomposed into two Lorentzian peaks (dash-dot-dash line). Summing the Lorentzian peaks (dashed line) produces a fit to the measured absorption spectrum (solid line).

FIG. 8 shows PLGA nanoparticle data for low pressures using data above to determine shift FIG. 9 shows 0.75 mg of Ag nanoparticles in chitosan at final concentration of 2.18% (w/v). Optical density vs. wavelength (entire curve not shown) was fit with two Lorentzian peaks. The high energy peak occurs at 757 nm. The low energy peak occurs at 826 nm.

Figure 10:
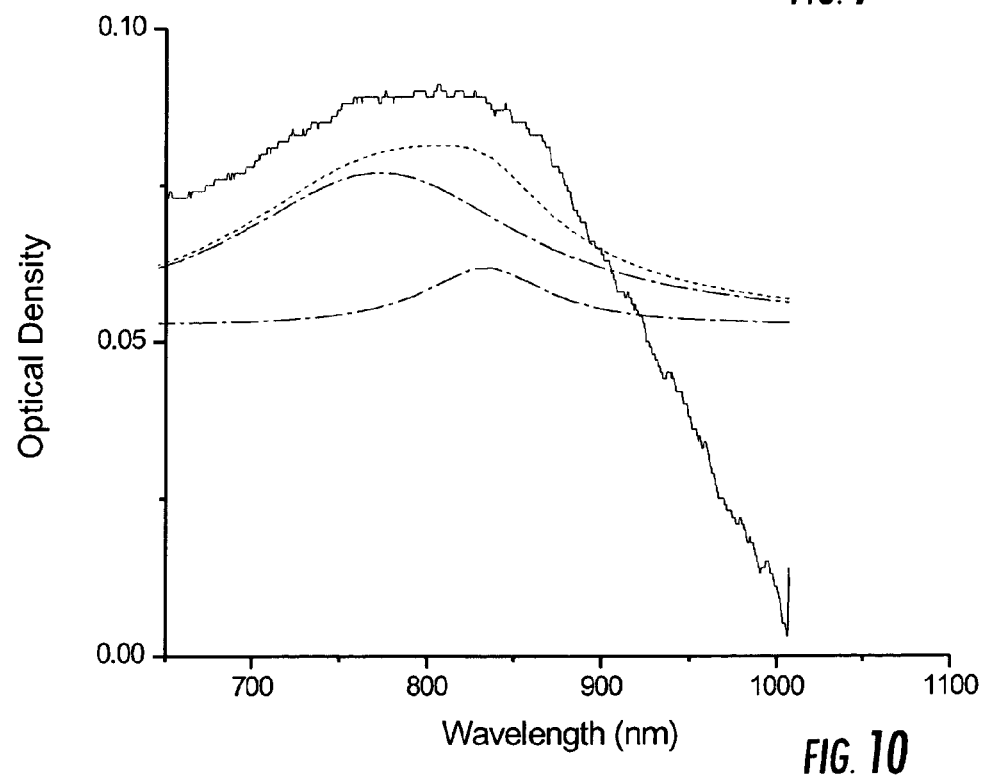
FIG. 10 is a graph of the optical density as a function of wavelength (nm) for 0.75 ml of Ag nanoparticles in chitosan at final concentration of 2.18% (w/v), with pressure applied (154 mmHg). The low energy peak was decomposed into two lorentzian peaks (dash-dot-dash lines), which when summed form the line fit (dotted line) to the entire peak (solid line).

FIG. 10 shows 0.75 ml of Ag nanoparticles in chitosan at final concentration of 2.18% (w/v). Pressure applied (154 mmHg). The high energy peak occurs at 773 nm. ($\Delta\lambda=16$ nm). The low energy peak occurs at 833 nm. ($\Delta\lambda=7$ nm).

Figure 11:
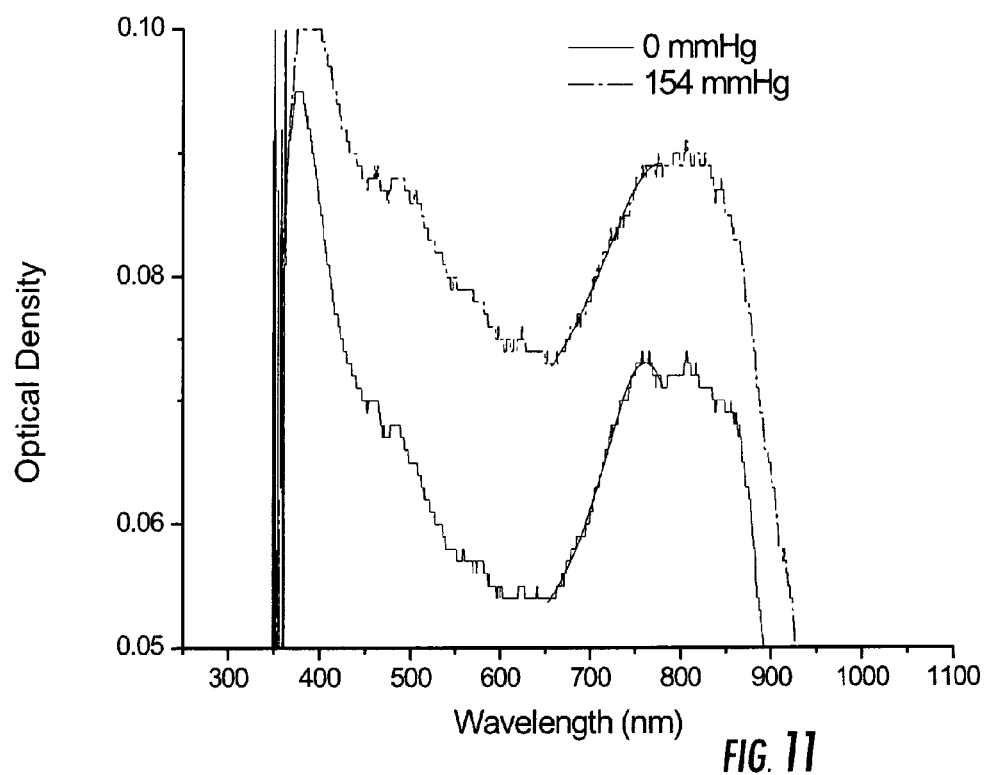
FIG. 11 is a graph of the optical density as a function of wavelength (nm) for 0.75 ml of Ag nanoparticles in chitosan at final concentration of 2.18% (w/v).

FIG. 11 shows 0.75 ml of Ag nanoparticles in chitosan at final concentration of 2.18% (w/v). Correlation coefficients improved (R2>0.99 for both curves) by fitting Lorentzian to only a selection of the data. 0 mmHg→762 nm; 154 mmHg→779 nm. $\Delta\lambda=17$ nm, almost same as doing multi-peak fit.

Figure 12:
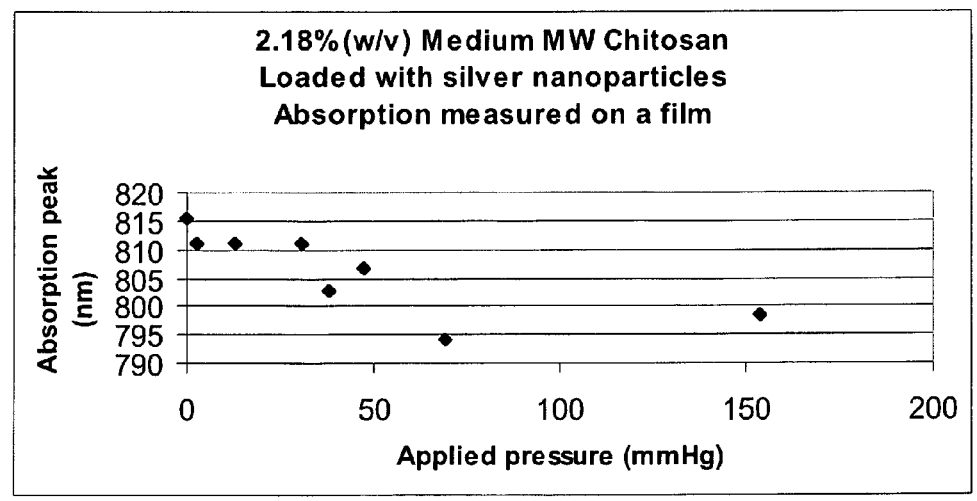
FIG. 12 is a graph of the absorption peak (nm) as a function of applied pressure (mm Hg) for 2.18% (w/v) medium MW chitosan loaded with silver nanoparticles on a film.

FIG. 12 shows 2.18% (w/v) medium MW chitosan loaded with silver nanoparticles. Absorption measured on a film. Absorption spectra collected with the Ocean Optics spectrometer were fit over the range 650-900 nm with three Lorentzian curves (Levenberg-Marquardt nonlinear curve fitting) since the feature of interest is observed in this range. Peak position was taken from the curve fit. According to the reduced chi square value (1.17197) and errors associated with all nine parameter for the Lorentzian fit, the curve fit is good.

Figure 13:
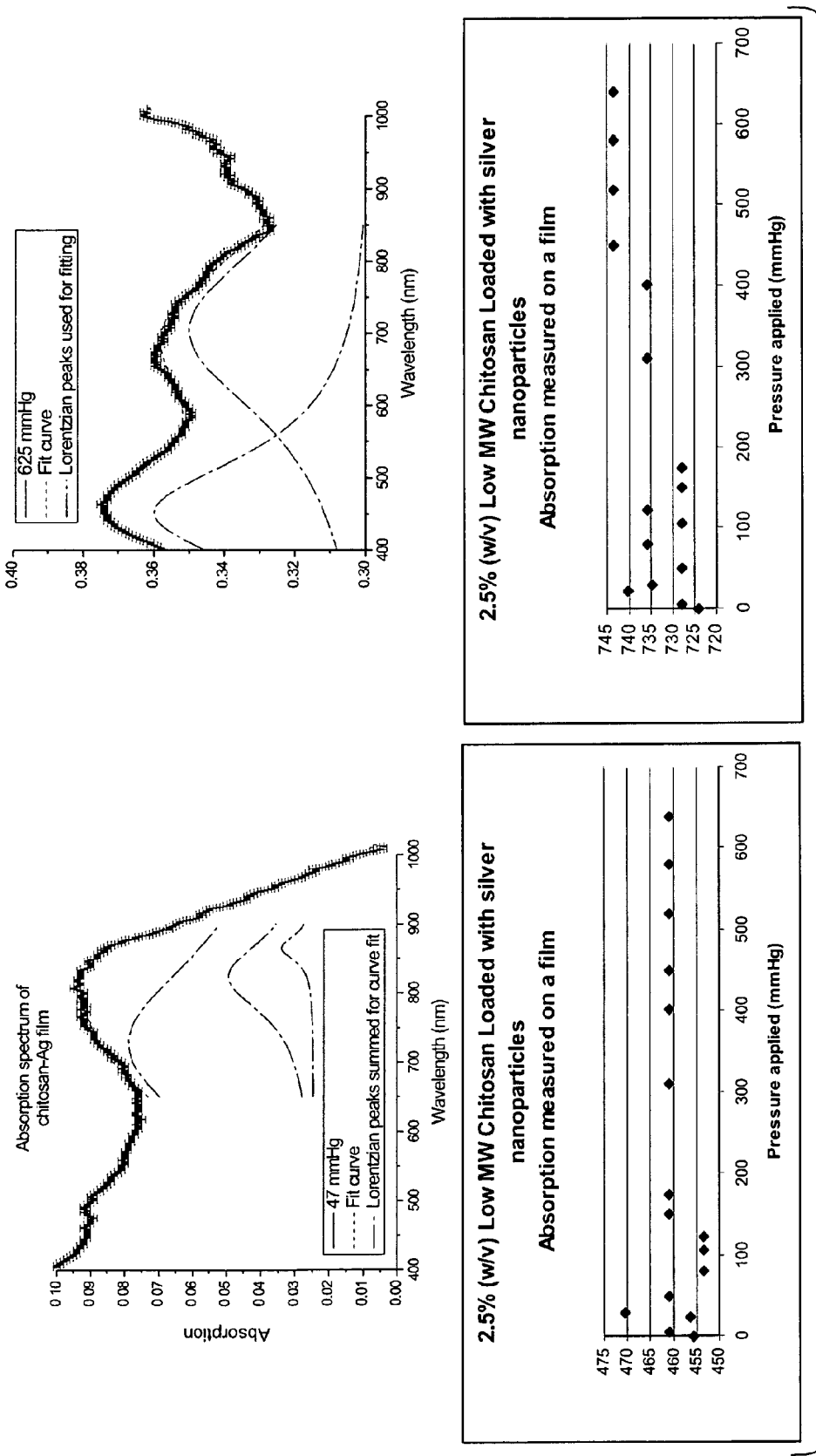
FIG. 13 are graphs of the absorption a function of wavelength (nm) (top graphs) and graphs of the peak absorption (nm) as a function of applied pressure (mm Hg) for (2.5% (w/v) low MW chitosan loaded with silver nanoparticles with absorption measured on a film.

FIG. 13. (2.5% (w/v) low MW chitosan loaded with silver nanoparticles absorption measured on a film.

Figure 18:
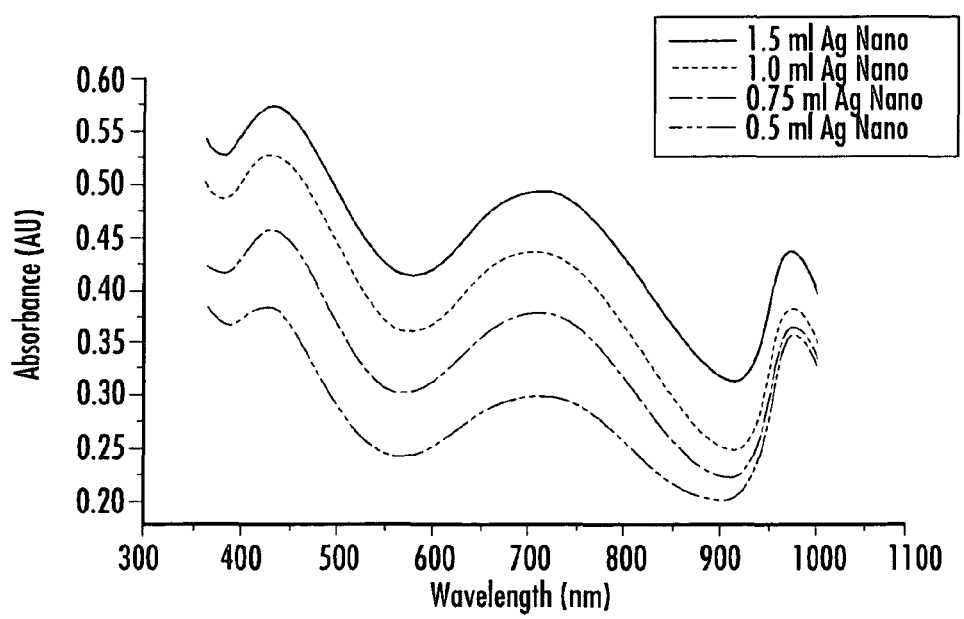
FIG. 18 is a graph of an absorbance spectra of chitosan/silver nanoparticle thin films at different concentrations on an optical fiber according to embodiments of the present invention.

FIG. 18 illustrates absorbance spectra of chitosan/silver nanoparticle thin films at different nanoparticle concentrations. This demonstrated success in synthesizing silver nanoparticles with characteristic absorbances in the near-IR range and achievement of adequate particle dispersion in the chitosan.

The functionality of the pressure sensors in "intensity mode" was determined by measuring the absorbance intensity at a single wavelength as the gas pressure in an experimental chamber was increased.

Figure 19:
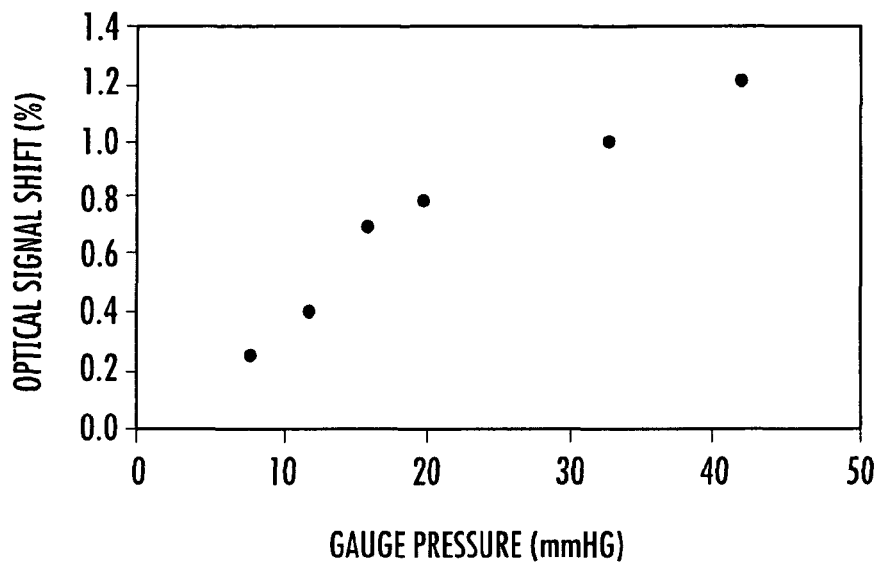
FIG. 19 is a graph of a sensor optical response (% signal shift) at increasing gauge pressures (mm Hg) on an optical fiber indicating a measurable increase in absorbance intensity with pressure increases.

FIG. 19 illustrates the sensor optical response at increasing gauge pressures indicating a measurable increase in absorbance intensity with subtle pressure increases. These data have a significant slope and indicate a correlatable relationship between the sensor's response and gauge pressure.

Adapting the polymer/nanoparticle composite to function in a "frequency mode" may also be desirable in some instances. While the absorbance intensity of the nanoparticles as measured by the spectrophotometer would generally be dependent on tissue depth in clinical use, a shift in the wavelength of peak intensity would generally be independent of this variable. This shift is typically dependent on the bulk modulus and dielectric constant of the polymer.

Figure 20:
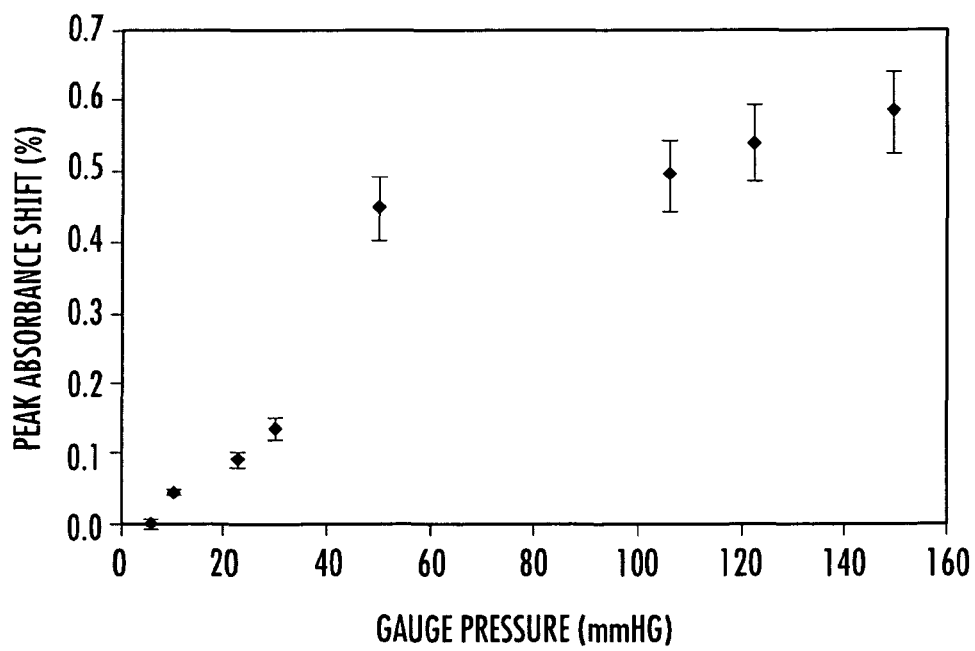
FIG. 20 is a graph of the peak absorbance shift (% signal shift) at increasing gauge pressures (mm Hg) on an optical fiber indicating a measurable shift in the peak absorbance wavelength with relatively subtle pressure increases.

FIG. 20 illustrates a peak absorbance shift at increasing gauge pressures indicating a measurable shift in the peak absorbance wavelength with subtle pressure increases. These data have a significant slope indicating a correlatable relationship between the sensor's shift in absorbance spectra in response to changes gauge pressure.

The foregoing is illustrative of the present invention, and is not to be construed as limiting thereof. The invention is defined by the following claims, with equivalents of the claims to be included therein.

That which is claimed is:

1. A method of sensing pressure in a region of interest, comprising:
   (a) providing one or more sensor particles in said region, each of said sensor particles comprising: (i) a polymer support and (ii) a plurality of metallic particles operatively associated with said polymer support and one another, wherein said metallic particles sustain a plasmon upon excitation, and with said metallic particles configured so that the energy of said plasmon varies in response to pressure;
   (b) measuring a physical property of said metallic particles that varies in response to pressure; and then
   (c) determining the pressure in said region of interest from said detected physical property,
   wherein said measuring step (b) is carried out by: (i) exciting said sensor particles to produce emitted light therefrom; (ii) detecting a property of said emitted light, wherein said property varies in response to said energy of said plasmon; and wherein: said determining step (c) is carried out by determining the pressure in said region of interest from said detected property.

2. The method of claim 1, wherein said property is the wavelength of emitted light, and wherein said wavelength of emitted light is from 2000 to 200 nanometers.

3. The method of claim 1, wherein said property is the intensity of emitted light.

4. The method of claim 1, wherein said metallic particles are from 1 nm to 1 micron in diameter.

5. The method of claim 1, wherein said pressure is from −5000 to 5000 torr.

6. The method of claim 1, wherein said metal is selected from the group consisting of silver, gold, platinum, copper, tungsten, titanium, palladium, and alloys thereof.

7. The method of claim 1, wherein said region of interest is in a human or animal subject, wherein said polymer support consists essentially of a pharmaceutically acceptable and bioerodable polymer, and wherein said metallic particles are pharmaceutically acceptable and excretable through the kidney of said subject.

8. The method of claim 1, wherein said region of interest is a tissue, airway space, vessel lumen, aneurism, embolism, or joint.

9. The method of claim 1, wherein said region of interest is a tissue compartment in a patient suspected of compartment syndrome.

10. The method of claim 1, wherein said region of interest is a wound site or region adjacent said wound site in a patient afflicted with said wound.

11. The method of claim 10, further comprising treating said wound with negative pressure wound therapy.

12. The method of claim 10, wherein said region of interest is a region adjacent a wound site and wherein said wound is treated with negative pressure wound therapy; said method further comprising: determining the presence or absence of pathological pressure at region adjacent said wound site from said determined pressure; and treating said region adjacent said wound site when a pathological pressure therein is determined.

13. The method of claim 10, said method further comprising: determining the pressure at said wound site or region adjacent said wound site to determine an actual wound pressure; and then adjusting vacuum applied to said wound in said negative pressure wound therapy in response to said actual wound pressure to enhance the efficacy of said negative pressure wound therapy.

14. A method of sensing pressure in a subject, comprising the steps of:
   (a) implanting a pressure-sensing biomedical implant in a region of interest in said subject, the biomedical implant comprising:
      (i) a biomedical implant substrate; and
      (ii) a plurality of metallic particles operatively associated with said substrate and one another, wherein said metallic particles sustain a plasmon upon excitation, and with said metallic particles configured so that the energy of said plasmon varies in response to pressure;
   (b) measuring a physical property of said metallic particles that varies in response to pressure; and then
   (c) determining the pressure in said region of interest from said detected physical property,
   wherein said measuring step (b) is carried out by: (i) exciting said sensor particles to produce emitted light therefrom; (ii) detecting a property of said emitted light, wherein said property varies in response to said energy of said plasmon; and wherein: said determining step (c) is carried out by determining the pressure in said region of interest from said detected property.

15. The method of claim 14, wherein said property is the wavelength of emitted light, and wherein said wavelength of emitted light is from 2000 to 200 nanometers.

16. The method of claim 14, wherein said property is the intensity of emitted light.

17. A method of sensing pressure on a pressure-sensing article produced by the process of coating an article with a pressure sensing coating composition, the pressure sensing coating composition comprising (a) a film-forming resin; (b) a solvent that disperses said resin; (c) one or more sensor particles dispersed therein; each of said sensor particles comprising: (i) a polymer support and (ii) a plurality of metallic particles operatively associated with said polymer support and one another, wherein said metallic particles sustain a plasmon upon excitation, and with said metallic particles configured so that the energy of said plasmon varies in response to pressure; and (c) optionally, at least one pigment, the method, comprising the steps of:

(a) exciting said sensor particles to produce emitted light therefrom;

(b) measuring a physical property of said metallic particles that varies in response to pressure; and then (c) determining the pressure in said region of interest from said detected physical property, wherein said measuring step (b) is carried out by: (i) exciting said sensor particles to produce emitted light therefrom; (ii) detecting a property of said emitted light, wherein said property varies in response to said energy of said plasmon; and wherein: said determining step (c) is carried out by determining the pressure in said region of interest from said detected property.

18. The method of claim 17, wherein said property is the wavelength of emitted light, and wherein said wavelength of emitted light is from 2000 to 200 nanometers.

19. The method of claim 17, wherein said property is the intensity of emitted light.

20. The method of claim 1, wherein said polymer support comprises a foam, a piezoelectric polymer, or a piezoelectric polymer foam.

* * * * *